United States Patent [19]

Saito et al.

[11] Patent Number: 4,987,548

[45] Date of Patent: Jan. 22, 1991

[54] ANALYZER OF PARTIAL MOLECULAR STRUCTURES

[75] Inventors: Keiji Saito, Yamaguchi; Katsuhiko Ichimura; Takahiro Tajima, both of Kyoto, all of Japan

[73] Assignee: Shimadzu Corporation, Yamaguchi, Japan

[21] Appl. No.: 214,439

[22] Filed: Jul. 1, 1988

[30] Foreign Application Priority Data

Jul. 4, 1987 [JP] Japan ............... 62-167486

[51] Int. Cl.$^5$ ............... G06F 15/46; G06F 15/42
[52] U.S. Cl. ............... 364/498; 364/582
[58] Field of Search ............ 364/497, 498, 582; 356/319, 326; 250/304, 340, 341

[56] References Cited

U.S. PATENT DOCUMENTS

| | | | |
|---|---|---|---|
| 4,093,991 | 6/1978 | Christie, Jr. et al. | 364/498 |
| 4,293,222 | 10/1981 | Caruso et al. | 364/498 |
| 4,357,673 | 11/1982 | Willis et al. | 364/582 |
| 4,365,303 | 12/1982 | Hannah et al. | 364/498 |
| 4,458,323 | 7/1984 | Willis et al. | 364/582 |
| 4,660,151 | 4/1987 | Chipman et al. | 364/498 |
| 4,719,582 | 1/1988 | Ishida et al. | 364/498 |

FOREIGN PATENT DOCUMENTS 0197804  4/1978  Canada ............... 364/582

OTHER PUBLICATIONS

"Digital Data Acquisition/Analysis System for Infrared Spectrophotometry"; LASL Optics Conf., 1979; Proc. Soc. Photo-Optic. Instrumentation; pp. 30-36.

Primary Examiner—Kevin J. Teska

[57] ABSTRACT

An analyzer of partial molecular structure analyzes a specimen material within an absorption spectrum. In addition to the wavenumber of peaks of an infrared absorption spectrum of a specimen, an analyzer analyzes molecules within partial structures using the strength of the peaks of the absorption spectrum so as to improve analysis accuracy.

16 Claims, 4 Drawing Sheets

ANALYZER OF PARTIAL MOLECULAR STRUCTURES

BACKGROUND OF THE INVENTION

The present invention relates to an analyzer of partial molecular structures of a specimen material within an infrared absorption spectrum and, more particularly, to an analyzer of partial molecular structures with reference to the strength of an infrared absorption spectrum.

An infrared spectroscopic analysis is to analyze a partial molecular structure. This analysis is achieved based on the position of an absorption peak (wavenumber) present in an infrared absorption spectrum obtained by an infrared spectrophotometer, so that a partial molecular structure corresponding to the wavenumber is analyzed as to whether it is contained in the molecule or not. Conventionally, information of the wavenumber of the absorption peak is taken out. However, the data amount of the wavenumber information is too limited to improve analysis accuracy. Further, the data of the wavenumber information on reference oscillation is obtained by superimposing the infrared absorption spectrum of materials with the same partial structure on the same graph. As the number of the materials to be examined increases to accumulate the data, high analysis accuracy could be expected. However, conventionally, it is difficult to accumulate new data on wavenumber data of the reference oscillation.

SUMMARY OF THE INVENTION

Accordingly, it is an object of the present invention to provide improved analyzer of a partial molecular structure for enhancing an analysis accuracy and accumulate data. It is another object of the present invention to provide an improved analyzer of a partial molecular structure for enhancing analysis accuracy by evaluating the strength of a peak of an absorption spectrum.

Briefly described, in accordance with the present invention, an analyzer for analyzing moleculars within partial structures, includes a data storage device for storing a wavenumber range, where peaks of an absorption spectrum of the partial structures appear, and the peaks of the absorption spectrum and absorption strength degrees, and a detection device for detecting one or more partial structures to be analyzed by detecting peaks of an infrared absorption spectrum of a specimen and comparing the wavenumber of all the absorption peaks with the wavenumber range where the peaks of the absorption spectrum of the partial structures appear, stored within the data storage device. It further includes a strength calculating device for calculating normalized strength degree of the absorption peaks of the specimen corresponding to the partial structures detected by the detection device and an evaluation factor calculating device for calculating evaluation factors between the strength of the absorption peaks calculated by the strength calculating device and the strength of the absorption peaks within the partial structures regarding one or more basic materials stored within the data storage device. Then score a determination device for determines the best score among the evaluation factors, regarding the one or more basic materials, within the partial structure, and an output device subsequently outputs the better scores of the partial structures.

BRIEF DESCRIPTION OF THE DRAWINGS

The present invention will become more fully understood from the detailed description given below and the accompanying drawings which are given by way of illustration only, and thus are not limitative of the present invention and wherein.

DESCRIPTION OF THE PREFERRED EMBODIMENT

Figure 2:
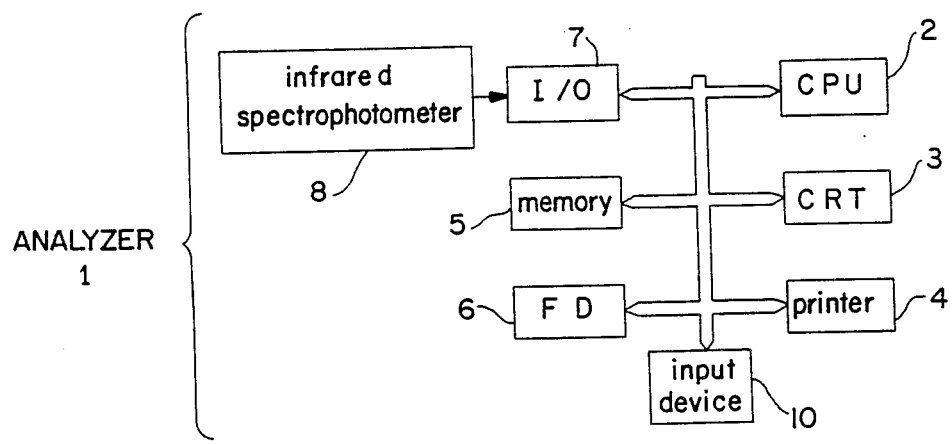
FIG. 2 is a block diagram of the analyzer.

An analyzer of a partial molecular structure according to a preferred embodiment will be described below. FIG. 2 shows a block diagram of a circuit implemented within an analyzer 1 of a partial molecular structure. A central processing unit (CPU) 2 is provided for conducting an analysis process as described below and for controlling the input/output of data. A cathode Ray Tube (CRT) 3, a printer 4, an input device 10 to input data to the CPU 2, and a memory 5 for storing data are connected to the CPU 2. A floppy disk device 6 is further connected to the CPU 2, as an auxiliary memory. Of course, instead of, or in addition to the floppy disk device 6, a hard disk device, a magnetic tape device, or an optical disk may be connected to the CPU 2.

Via an input/output device 7, an infrared spectrophotometer 8 is connected to the CPU 2. An infrared absorption spectrum measured by the infrared spectrophotometer 8 is transmitted to the CPU 2.

Figure 1A:
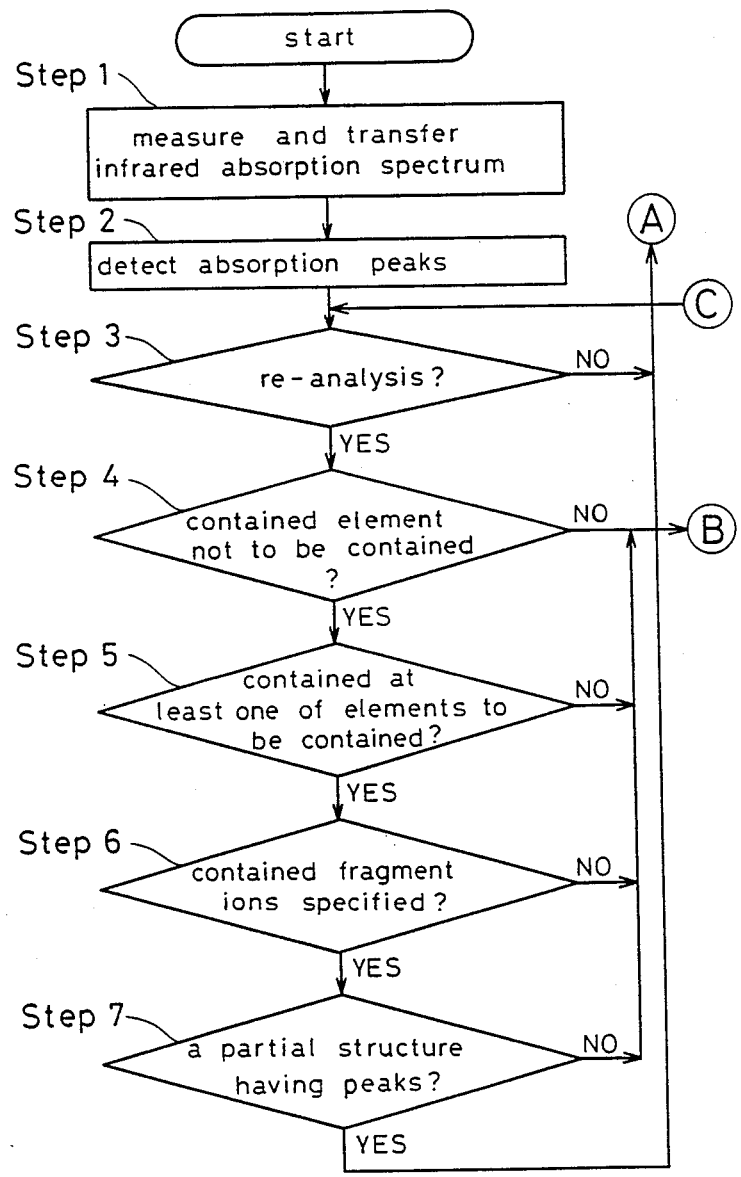
FIG. 1 (a) and FIG. 1 (b) are flow chart showing the operation of an analyzer of a partial molecular structure according to a preferred embodiment of the present invention.
Figure 1B:
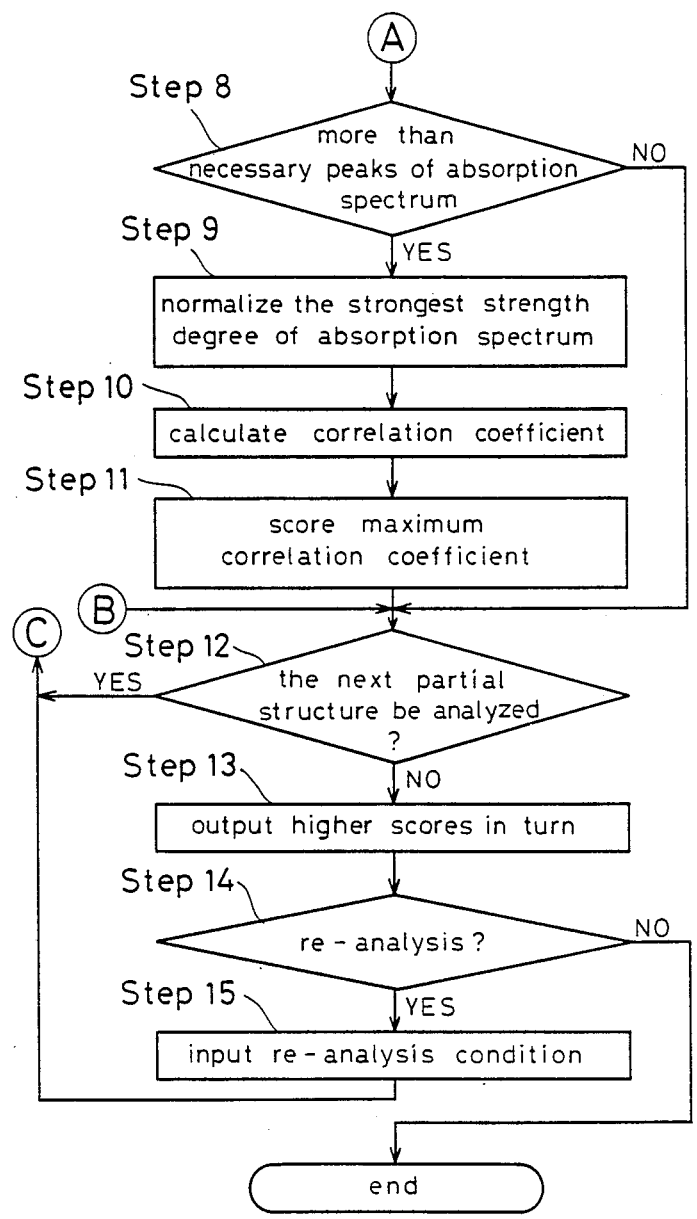

Now, the operation of the analyzer 1 will be described with reference to FIG. 1 (a) and FIG. 1 (b) showing its flow chart.

Figure 3:
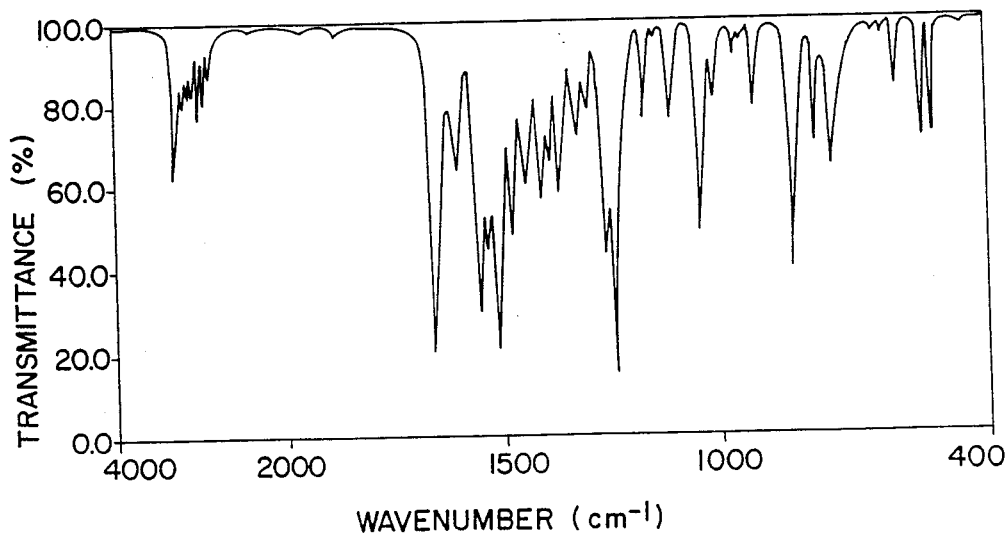
FIG. 3 is an infrared absorption spectrum of phenacetin obtained by an infrared spectrophotometer of the analyzer.

Step 1: A specimen is set in the infrared spectrophotometer 8 to measure an infrared absorption spectrum and transmit the spectrum to the CPU 2. An example of such infrared absorption spectrum is illustrated in FIG. 3, showing a spectrum of phenacetin ($CH_3$—CO—NH—$C_6H_4$—O—$C_2H_5$) measured by a diffused reflection method.

Figure 4:
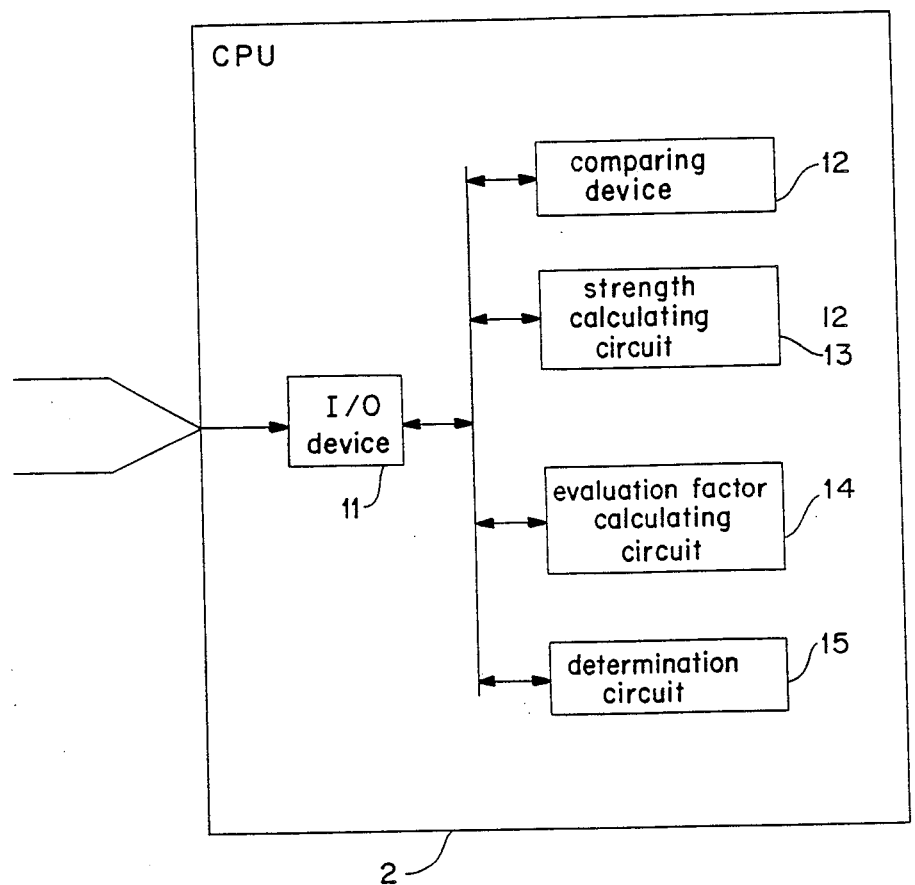
FIG. 4 is a block diagram of the CPU 2.

The measured infrared absorption spectrum is then normalized by strength calculating circuit 13 of FIG. 4 to cancel error due to density. The normalization is calculated by transferring the spectrum with absorption, so that minimum absorption of the spectrum is set to be "0" while maximum of absorption of the spectrum is set to be "99".

Step 2: The wavenumber ($cm^{-1}$) at the peak of absorption in the spectrum and the strength at the peak are obtained and listed. Table 1 shows an example.

TABLE 1

| Data; the measured data at the peaks Peak Information | | |
|---|---|---|
| S 328524, | 165980, | 155754, |
| 153731, | 151171, | 148328, |
| 126738, | 124894, | 104835, |
| 083846, | 082830, | |
| M 319008, | 313508, | 307508, |
| 298513, | 293007, | 160518, |
| 144815, | 141418, | 139409, |
| 137017, | 132608, | 117612, |

TABLE 1-continued

Data; the measured data at the peaks
Peak Information

| | | |
|---|---|---|
| 111613, | 102008, | 092411, |
| 078514, | 074519, | 060609, |
| 054816, | 052315, | |

In Table 1, "S" represents "Strong Peak", such that "S 328524" indicates that the peak of a strength degree 24 lies at a wavenumber 3285 cm$^{-1}$. "M" represents "Medium Peak", such that "M 319008" indicates that the peak of a strength degree 08 lies at a wavenumber 3190 cm$^{-1}$. In Table 1, "Strong Peak" is referred to when a strength degree is equal to or more than 20 while "Medium Peak" is referred to when a strength degree is equal to or less than 19, but equal to or more than 5.

Step 3; This step is used to determine a re-analysis or not. First it will be explained when no re-analysis procedure is conducted, so the process advances to step 8.

Step 8: This step is used to determine whether a re-analysis is needed or not. Absorption spectrum of a specimen are present or not by determining whether the number of peaks are equal to or more than a predetermined number, the predetermined number being a range wherein every partial molecular structure has a wavenumber range. This determination is carried out by the comparing device 12 of FIG. 4. "NO" determination at step 8 indicates that there is little probability that the partial structure exists. Then, the analysis ends and the process advances to step 12. A "YES" determination at step 8 indicates that there is probability that the partial structure exists and the process advances to step 9 and the following analysis steps.

Table 2 shows an example of a wavenumber range on

(1,4-disubst benzene). In Table 2, "st" indicates stretching "ω" indicates out-of-plane bending or wagging, and "d" indicates a deformation.

TABLE 2

| Wavenumber region (cm$^{-1}$) | Attribution | |
|---|---|---|
| 3100~3000 | CH | st |
| 1520~1500 | C—C | st |
| 1460~1440 | C—C | st |
| 860~800 | CH | ω |
| 730~670 | ring | d |

Step 9: This step is used to normalize the strength degree of the peaks of the absorption spectrum with the strongest strength degree of the peak of the absorption spectrum. This normalization is carried out by the strength calculating circuit 13 of FIG. 4. Table 3 shows an example on

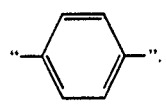

Table 3 shows the strength ratio on three basic materials of the data stored within the memory 5.

TABLE 3

| Wavenumber region (cm$^{-1}$) | Strength ratio of specimen | Strength degree (wavenumber) of basic materials | | |
|---|---|---|---|---|
| | | I | II | III |
| 3100~3000 | 11 | 29 (3020) | 10 (3070) | 11 (3040) |
| 1520~1500 | 99 | 55 (1515) | 76 (1510) | 99 (1510) |
| 1460~1440 | 21 | 30 (1460) | 24 (1455) | 35 (1555) |
| 860~800 | 42 | 99 (815) | 99 (845) | 69 (810) |
| 730~670 | 0 | 11 (720) | 37 (740) | 46 (680) |

Step 10: This step is to calculate a correlation coefficient R, calculated in the evaluation factor circuit 14 of FIG. 4, as an evaluation factor based on the strength ratio obtained at step 9 according to the following equation.

$$R = \frac{\sum_i (Xi - \overline{X}) \cdot (Yi - \overline{Y})}{\left\{ \sum_i (Xi - \overline{X})^2 \cdot \sum_i (Yi - \overline{Y})^2 \right\}^{\frac{1}{2}}}$$

Where
i: the serial number of an absorption peak
Xi: the absorption peak strength ratio (absorbance) of a basic material
Yi: the absorption peak strength ratio (absorbance) of a specimen material
$\overline{X}$: the average of the absorption peak strength ratio (absorbance) of the basic materials
$\overline{Y}$: the average of the absorption peak strength ratio (absorbance) of the specimen material When data for a plurality of kinds of basic materials are present about a single partial molecular structure, the correlation coefficient R is calculated for everyone of the basic materials. As to the example shown in Table 3, the correlation coefficient R is calculated for three basic materials. If there is a basic material whose peak of the absorption spectrum is not within a predetermined wavenumber region, the strength degree of the peak of the absorption spectrum is set to be "0".

As the correlation coefficient R increases, there is higher probability that the partial structure exists. The evaluation factors are calculated using the following two equations alternatively. In this case, if the factors of the formulae decrease there is higher probability that the partial structure exists.

$$R' = \frac{\sum_i |Xi - Yi|}{n}$$

$$R'' = \frac{\left( \sum_i (Xi - Yi)^2 \right)^{\frac{1}{2}}}{n}$$

Where n: the number of the peaks of the absorption spectrum.

Step 11: This step is used to extract the maximum among one or more correlation coefficients R calculated at step 10, so that the maximum is scored as "S" in the related partial structure. This process is carried out by the determination circuit 15 of FIG. 4.

Step 12: This step is used to determine whether the next partial structure is analyzed or not. When all of the partial structures are analyzed, step 13 is selected.

Step 13: In this step, the CRT 3 and or the printer 4 is operated to output all the partial structures in the sequence of the greater scores S. That is, the partial structures with the greater probability of existence are in turn outputted.

Step 14: This step is used to modify the analysis conditions on the same specimen and determine whether a re-analysis process should be conducted or not. For a re-analysis process, step 15 is selected. If no re-analysis process is selected, the analysis has been completed.

Step 15: This step is used to input new analysis conditions for a re-analysis process. The analysis conditions are as follows:

(1) selection of a specific peak in an absorption spectrum (Only a partial structure containing the selected peak is outputted);

(2) input of the results (fragment ion) obtained by mass analysis (Only a partial structure containing the selected fragment ion is outputted);

(3) input of chemical elements being present (Only a partial structure containing at least one of the inputted elements is outputted);

(4) input of chemical elements not being present (Only a partial structure containing none of the inputted elements is outputted);

(5) alteration of a wavenumber and its strength degree (After the wavenumber and the strength degree detected based on its peak data are erased, added, or altered, re-analysis process is conducted);

Thus, additional information such as the results obtained with analysis other than the infrared spectrum analysis, may be included as the analysis conditions, so as to focus on the partial structure to be analyzed, thus shortening the analysis time period.

After the analysis conditions are inputted and altered, steps 4 to 7 are selected to conduct a process using the inputted analysis conditions.

Step 4: This step is used to determine whether the chemical elements, inputted as not being present, are contained within the partial structures or not. If they are not contained, step 5 and the subsequent steps are selected. If contained, step 12 is selected to analyze the next partial structure because it is not possible for the elements to be present within the partial structure.

Step 5: This step is used to determine whether at least one of chemical elements inputted as presence is contained within the partial structure or not. If present, step 6 and the subsequent steps are selected. If not, step 12 is selected to analyze the next partial structure because it is not possible for the elements not to be present within the partial structure.

Step 6: This step 6 is selected to determine whether the fragment ion considered to be present, which are detected by the mass analyzer, is contained within the partial structure or not. If present, step 7 and the subsequent steps are selected. If not, step 12 is selected to analyze the next partial structure since it is not possible for the elements to be present within the partial structure.

Step 7: This step is used to determine whether or not the partial structure contains a peak of the absorption spectrum within a selected specific range of a wavenumber. If contained, step 8 and the subsequent steps are advanced. If not, step 12 is selected to analyze the next partial structure since it is not possible for the present partial structure to contain it.

Step 8 and the subsequent steps are as described below. Steps 4 to 7 are used to analyze the information including the additional information, rather than the infrared spectrum. The process of step 7 can make it possible to analyze, in turn, each one of peaks of an absorption spectrum to be analyzed.

It is possible to input the re-analysis condition of step 15 after the process of step 2 and at the start of the analysis. In case where a spectrum chart obtained by measuring an infrared absorption spectrum is present, the information of the absorption peak can be directly inputted into a computer, without measuring at step 1. The measured data are stored into a data base for analyzing the partial structure.

As described above, in accordance with the present invention, the partial structure analyzer can evaluate the strength degree of an absorption peak to improve analysis accuracy. The specimen data can be stored into a data storage means as the data for basic materials, so that the accumulated data can improve analysis accuracy. Since the information inclusive of the additional information rather than the infrared spectrum is used for analysis, the partial structure to be analyzed can be focused to shorten analysis time period. In addition to the wavenumber of the peaks of an infrared absorption spectrum of a specimen, the analyzer of the present invention analyzes moleculars within partial structures using the strength of the peaks of the absorption spectrum so as to improve analysis accuracy.

While only certain embodiments of the present invention have been described, it will be apparent to those skilled in the art that various changes and modifications may be made therein without departing from the spirit and scope of the present invention as claimed.

What is claimed is:

1. An analyzer for analyzing molecular structures within a specimen, comprising:

spectrophotometer means for producing an absorption spectrum data set of a specimen wherein the specimen has a partial molecular structure, said absorption spectrum data set having peaks of an absorption spectrum and associated absorption strength degrees;

data storage means for storing a wavenumber range, reference peaks of an absorption spectrum and reference absorption strength degrees associated with said peaks of the absorption spectrum, said reference peaks being within said wavenumber range;

analyzing means, operatively connected to said data storage means and said spectrophotometer means, for comparing wavenumbers of all said absorption peaks of the specimen with said wavenumber range stored within said data storage means to determine if said wavenumbers are within said wavenumber range, for calculating normalized strength degree of the absorption peaks of the specimen corresponding to said absorption spectrum data set produced by said spectrophotometer means, for calculating evaluation factors between said normalized strength degree of the absorption peaks of the specimen and said reference absorption strength degree stored within said data storage means, and for determining if a partial molecular structure is present within the specimen according to said evaluation factors; and output means, operatively connected to said analyzing means, for outputting information regarding the partial molecular structures present within the specimen.

2. The analyzer as claimed in claim 1, further comprising:
memory means for storing wavenumbers of said absorption peaks of the specimen and the associated strength degree of said absorption peaks when the wavenumbers and the strength degree are suitable as future reference data.

3. The analyzer as claimed in claim 1, wherein said spectrophotometer means is an infrared spectrophotometer.

4. The analyzer as claimed in claim 1, further comprising:
input means for inputting analysis results analyzed by a second analyzer;
said analyzing means, responsive to said input means, carrying out a full analysis using said analysis results inputted through said input means as said reference peaks of the absorption spectrum and said reference absorption strength degrees.

5. The analyzer as claimed in claim 4, wherein said second analyzer is a mass spectrophotometer.

6. An analyzer for analyzing partial molecular structures of a specimen, comprising:
spectra data generating means for generating spectra data from a specimen being tested, said spectra data including at least a range of wavenumbers and absorption strength degrees for each wavenumber;
comparator means, operatively connected to said spectra-data generating means, for comparing said range of wavenumbers with a predetermined wavenumber range to determine whether said range of wavenumbers is within said predetermined wavenumber range;
normalizing means, responsive to said comparator means, for normalizing said absorption strength degrees;
correlation means, operatively connected to said normalizing means, for calculating evaluation factors between the normalized absorption strength degrees and predetermined absorption strength degrees of a known partial molecular structure; and
determination means, operatively connected to said correlation means, for determining if the specimen contains the known partial molecular structure according to said evaluation factors.

7. The analyzer as claimed in claim 6 further comprising:
output means, operatively connected to said determination means, for outputting information regarding the determination of the partial molecular structure within the specimen.

8. The analyzer as claimed in claim 6 further comprising:
storage means, operatively connected to said comparator means and said correlation means, for storing said predetermined wavenumber range and said predetermined absorption strength degrees.

9. The analyzer as claimed in claim 6, wherein said spectra data also include data representing peaks of an absorption spectrum, said data being associated with said absorption strength degrees.

10. The analyzer as claimed in claim 6, wherein aid spectra data generating means is an infrared spectrophotometer.

11. The analyzer as claimed in claim 6 further comprising:
input means, operatively connected to said comparator means and said correlation means, for inputting said predetermined wavenumber range and said predetermined absorption strength degrees.

12. The analyzer as claimed in claim 11, wherein said input means is a mass spectrophotometer.

13. A method for analyzing partial molecular structures, comprising the steps of:
obtaining spectra data from a specimen being tested by a spectrophotometer, the spectra data including a range of wavenumbers, data representing peaks of an absorption spectrum and absorption strength degrees of each peak of the absorption spectrum;
comparing the range of wavenumbers with a predetermined wavenumber range to generate a comparison result;
determining from the comparison result generated in said comparing step if the range of wavenumbers is within the predetermined wavenumber range;
normalizing the absorption strength degrees when the determination of said determining step is positive;
generating evaluation factors between the normalized absorption strength degrees and predetermined absorption strength degrees of a known partial molecular structure;
ascertaining if the specimen contains known partial molecular structures according to the evaluation factors previously generated; and
producing information indicating the known partial molecular structures previously ascertained to be contained within the specimen.

14. The method as claimed in claim 13, further comprising the step of:
outputting the information produced in said producing step.

15. The method as claimed in claim 13, further comprising the step of:
prestoring the predetermined wavenumber range and the predetermined absorption strength degrees in a memory device.

16. The method as claimed in claim 13 further comprising the step of:
inputting the predetermined wavenumber range and the predetermined absorption strength degrees through a second analyzer wherein the second analyzer is a mass spectrophotometer.

* * * * *

UNITED STATES PATENT AND TRADEMARK OFFICE
CERTIFICATE OF CORRECTION

PATENT NO. : 4,987,548
DATED : January 22, 1991
INVENTOR(S) : Keiji SAITO, Katsuhiko ICHIMURA and Takahiro TAJIMA It is certified that error appears in the above-identified patent and that said Letters Patent is hereby corrected as shown below:

On the title page, item [73]

Please correct the Assignee portion of the above-identified issued Patent to read as follows:

Change "Shimadzu Corporation, Yamaguchi, Japan" to --Shimadzu Corporation, Kyoto, Japan and UBE Industries Ltd., Yamaguchi, Japan--

Signed and Sealed this

Twenty-eighth Day of July, 1992

Attest:

DOUGLAS B. COMER

*Attesting Officer*     *Acting Commissioner of Patents and Trademarks*